United States Patent
Smokvina et al.

(10) Patent No.: US 9,297,049 B2
(45) Date of Patent: Mar. 29, 2016

(54) **STRAIN OF *LACTOBACILLUS MUCOSAE***

(75) Inventors: Tamara Smokvina, Orsay (FR);
Marie-Christine Degivry, Le Plessis Robinson (FR)

(73) Assignee: Compagnie Gervais Danone, Paris (FR)

( * ) Notice: Subject to any disclaimer, the term of this patent is extended or adjusted under 35 U.S.C. 154(b) by 0 days.

(21) Appl. No.: 14/366,745

(22) PCT Filed: Dec. 21, 2011

(86) PCT No.: PCT/IB2011/055876
§ 371 (c)(1),
(2), (4) Date: Jul. 8, 2014

(87) PCT Pub. No.: WO2013/093561
PCT Pub. Date: Jun. 27, 2013

(65) Prior Publication Data
US 2014/0328802 A1    Nov. 6, 2014

(51) Int. Cl.
*C12N 1/20*     (2006.01)
*C12R 1/225*    (2006.01)
*A23L 1/30*     (2006.01)
*A61K 35/744*   (2015.01)
*C12N 15/74*    (2006.01)
*A61K 35/00*    (2006.01)

(52) U.S. Cl.
CPC ................ *C12R 1/225* (2013.01); *A23L 1/3014* (2013.01); *A61K 35/744* (2013.01); *C12N 1/20* (2013.01); *C12N 15/746* (2013.01); *A61K 35/00* (2013.01)

(58) Field of Classification Search
None
See application file for complete search history.

(56) References Cited

FOREIGN PATENT DOCUMENTS

WO    2011/107960 A1    9/2011

OTHER PUBLICATIONS

International Search Report and Written Opinion issued in corresponding International Patent Application No. PCT/IB/2011/055876 dated Mar. 2, 2012.
Eun et al., "Lactobacillus casei prevents impaired barrier function in intestinal epithelial cells," APMIS, 119: 49-56 (2011).
Miyauchi et al., "Lactobacillus rhamnosus alleviates intestinal barrier dysfunction in part by increasing expression of zonula occludens-1 and myosin light-chain kinase in vivo," Journal of Dairy Science, American Dairy Science Association, 92: 2400-2408 (2009).
Tzortzis et al., "Modulation of anti-pathogenic activity in canine-derived Lactobacillus species by carbohydrate growth substrate," Journal of Applied Microbiology, 96: 552-559 (2004).
Roos et al., "*Lactobacillus mucosae* sp. nov., a new species with in vitro mucus-binding activity isolated from pig intestine," International Journal of Systematic and Evolutionary Microbiology, 50: 251-258 (2000).

*Primary Examiner* — Jennifer Graser
(74) *Attorney, Agent, or Firm* — Morgan, Lewis & Bockius LLP

(57) ABSTRACT

The invention relates to a new strain of *Lactobacillus mucosae* which is able to decrease intestinal barrier permeability. This strain is useful in particular for alleviating intestinal barrier dysfunctions.

4 Claims, 3 Drawing Sheets

A

B

C

D

STRAIN OF *LACTOBACILLUS MUCOSAE*

The invention relates to a novel strain of *Lactobacillus mucosae* and its uses, in particular for alleviating intestinal barrier dysfunctions.

The intestinal epithelium acts as a defensive barrier protecting the mucosal surface against luminal contents and the external environment.

The intestinal epithelial layer has a low level of permeability due to the presence of tight junctions (TJs) between the cells. Tight junctions are intercellular complexes that function as a barrier limiting the transfer of materials from the intestinal lumen into the intestinal mucosa. Disruption of these complexes can be induced by exogenous factors such as some enteric pathogens, or by pro-inflammatory cytokines, including in particular TNF-α and IFN-γ; it leads to increased epithelial paracellular permeability, which contributes to various intestinal disorders, including in particular irritable bowel syndrome, chronic inflammatory bowel diseases (Crohn's disease or ulcerative colitis), and celiac disease (for review, see (CLAYBURGH et al., Lab Invest, 84, 282-91, 2004).

Various probiotic lactic acid bacteria are known to have protective effects on intestinal epithelium, through different mechanisms (for review see (OHLAND & MACNAUGHTON, American Journal of Physiology—Gastrointestinal and Liver Physiology, 298, G807-G19, 2010). However, only some strains of a few species have been shown as improving epithelial barrier function through decreasing its permeability. (RESTA-LENERT & BARRETT, Gastroenterology, 130, 731-46, 2006) report that *Streptococcus thermophilus* and *Lactobacillus acidophilus* prevented the increase of epithelial permeability induced by TNF-α and IFN-γ. (MIYAUCHI et al., J Dairy Sci, 92, 2400-8, 2009) studied the effects of 4 lactobacilli (one strain of *L. delbrueckii*, one strain of *L. casei*, one strain of *L. gasseri*, and *L. rhamnosus* strain OLL2838) on impaired intestinal barrier function and paracellular permeability induced by TNF-α. They found that *L. rhamnosus* OLL2838 significantly suppressed the TNF-α-induced increase of paracellular permeability, while the other tested strains had no significant effects. (DONATO et al., Microbiology, 156, 3288-97, 2010) showed that *L. rhamnosus* strain LGG alleviated the effects of TNF-α or IFN-γ on epithelial barrier integrity. (EUN et al., Apmis, 119, 49-56, 2010) showed that *L. casei* strain DN 114001 (CNCM I-1518) also prevented the increase of epithelial permeability induced by TNF-α or IFN-γ. Z. ZAKOSTELSKA et al recently reported that the lysate of *Lactobacillus paracasei* DN-114001 (CNCM I-1518) strengths the integrity of gut cellular barrier in vivo (ZAKOSTELSKA et al, 2011. PlosOne 6(11).

*Lactobacillus mucosae* was isolated for the first time from pig small intestine, and later was also isolated from human intestine and vagina, as well as from dog's, calve's and horse's intestine.

It was first characterized as a species by ROOS and his collaborators (ROOS et al., Int J Syst Evol Microbiol, 50 Pt 1, 251-8, 2000). Taxonomically, *Lactobacillus mucosae* is closely related to *Lactobacillus fermentum, Lactobacillus reuteri* and *Lactobacillus pontis*. It contains the mub gene, encoding a cell-surface protein which gives it mucus-binding ability. ROOS et al. described it as Gram-positive, catalase negative, non spore-forming, non-motile rods, growing in 45° C. but not in 15° C.

Some strains of *Lactobacillus mucosae* have been shown to possess anti-microbial activity. TZORTIS al. (TZORTZIS et al., J Appl Microbiol, 96, 552-9, 2004) reports that the strain NCIMB 41149 of *L. mucosae* has in vitro inhibitory activity on *Echerichia coli* and *Salmonella typhymurium* when grown in the presence of malto-oligosaccharide or maltose, but not in the presence of glucose, isomalto-oligosaccharides, gentiobiose or cellobiose. PCT application WO 2011/107960 describes the use of *L. mucosae* strains DSM23409 and DSM23408 for treatment or prevention of *E. coli* infections.

Until now, no effect of any strain of the species *Lactobacillus mucosae* on intestinal barrier function has been reported.

Figure 1:
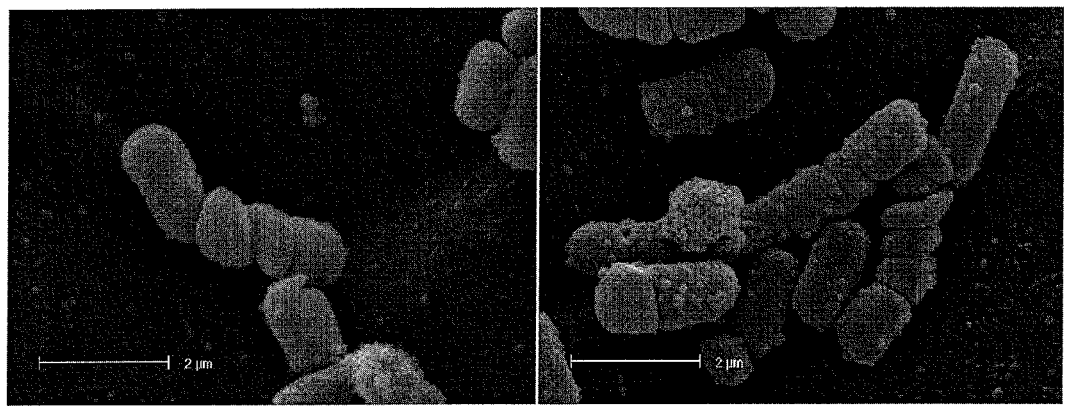
FIG. 1: Electron microscopy images of strain CNCM I-4429.

The inventors have now identified a new *Lactobacillus mucosae* strain, which besides anti-microbial activity, has the ability of improving intestinal barrier function, in particular by decreasing intestinal epithelial permeability.

A subject of the present invention is this strain, which was deposited, according to the Treaty of Budapest, with the CNCM (Collection Nationale de Cultures de Microorganismes, 25 rue du Docteur Roux, Paris), on February 3, 2011, under number I-4429.

The CNCM I-4429 strain is a gram-positive, catalase-negative microorganism, non-motile, non-spore forming; the cells occur as rods with dimensions of 1×2-4 μm, isolated in pairs or as small chains.

It has antimicrobial properties and in particular strongly inhibits the growth of *Salmonella enterica*.

It also has the property of decreasing intestinal barrier permeability, in other words of protecting or restoring the epithelial paracellular imperviousness, and in particular the property of preventing or reverting the increase of epithelial paracellular permeability induced by TNF-α.

The subject of the present invention also encompasses *Lactobacillus mucosae* strains that can be obtained by mutagenesis or by genetic transformation of the CNCM I-4429 strain. Preferably, these strains retain the properties of the CNCM I-4429 strain on decreasing intestinal barrier permeability. They may be strains in which one or more of the endogenous genes of the CNCM I-4429 strain has (have) been mutated, for example so as to modify some of its metabolic properties (e.g. the ability of this strain to metabolize sugars, its resistance to intestinal transit, its resistance to acidity, its post-acidification or its metabolite production). They may also be strains resulting from genetic transformation of the CNCM I-4429 strain with one or more gene(s) of interest, making it possible, for example, to confer additional physiological characteristics on said strain, or to express proteins of therapeutic or vaccine interest, which it is desired to administer by means of said strain.

These strains can be obtained from the CNCM I-4429 strain by means of the conventional techniques for random or site-directed mutagenesis and genetic transformation of lactobacilli, such as those described, for example, by GURY et al. (Arch Microbiol., 182, 337-45, 2004) or by VELEZ et al. (Appl Environ Microbiol., 73, 3595-3604, 2007), or by the technique known as "genome shuffling" (PATNAIK et al. Nat Biotechnol, 20, 707-12, 2002; WANG Y. et al., J Biotechnol., 129, 510-15, 2007).

A subject of the present invention is also a method for obtaining a *Lactobacillus mucosae* strain able to decrease intestinal barrier permeability, comprising a step of mutagenesis or of genetic transformation of the CNCM I-4429 strain.

A subject of the present invention is also a method for obtaining a cell fraction able to decrease intestinal barrier permeability, from a *Lactobacillus mucosae* strain in accordance with the invention. Said cell fractions are in particular DNA preparations or bacterial wall preparations obtained from cultures of said strain. They may also be culture supernatants or fractions of these supernatants.

A subject of the present invention is also compositions comprising a *Lactobacillus mucosae* strain in accordance with the invention or a *Lactobacillus mucosae* strain that can be obtained by mutagenesis or by genetic transformation of the CNCM I-4429 strain or a cell fraction obtained from said strain.

These compositions can in particular be lactic ferments, combining a *Lactobacillus mucosae* strain in accordance with the invention with one or more other, optionally probiotic, strain(s) of lactic acid bacteria. By way of example of strains of lactic acid bacteria, mention may be made from the genera *Lactobacillus*, *Streptococcus*, *Lactococcus*, and *Bifidobacterium*, in particular *Lactobacillus bulgaricus*, *Streptococcus thermophilus* strains, *L. acidophilus*, *L. casei*, *L. plantarum*, *L. reuteri*, *L. johnsonii*, *L. rhamnosus*, *Lactobacillus casei* ssp. *paracasei* strains.

They may also be food products, and in particular dairy products, or pharmaceutical or cosmetic products comprising a *Lactobacillus mucosae* strain in accordance with the invention, or a *Lactobacillus mucosae* strain obtained by mutagenesis or by genetic transformation of the CNCM I-4429 strain or a cell fraction obtained from said strain.

When said strain is present in the form of live bacteria, they will preferably be present in a proportion of at least $10^5$ cfu per gram, advantageously at least $10^6$ cfu per gram of product, more advantageously at least $10^7$ cfu per gram, and even more advantageously at least $10^8$ cfu per gram.

A subject of the present invention is also a method for obtaining a composition as described above, characterized in that it comprises:
- obtaining a *Lactobacillus mucosae* in accordance with the invention or a *Lactobacillus mucosae* strain obtainable by the method described above, or a cell fraction in accordance with the invention and
- incorporating said strain or fraction into said composition.

The *Lactobacillus mucosae* strains, cell fractions, and compositions of the invention can be used in the treatment or prevention of conditions involving intestinal barrier dysfunctions, in particular conditions associated with an increase of intestinal barrier permeability.

The present invention will be understood more clearly from the further description which follows, which refers to examples illustrating the characterization and properties of the *Lactobacillus mucosae* strain CNCM I-4429.

EXAMPLE 1

Morphology and Fermentation Properties of *Lactobacillus Mucosae* Strain CNCM I-4429

Morphology

Electron microscopy images of strain CNCM I-4429 are shown on FIG. 1. The strain CNCM I-4429 appears in twisted shape; it is a twisted *bacillus*

Analysis of the Carbohydrate Metabolism:

The analysis of sugars fermentation were performed on Bioscreen apparatus (Oy Growth Curves Ab Ltd). For the analysis 21 sugars were selected. They are listed in Table I. The assay performed in Bioscreen lasted twenty-four hours, the measurement were performed each 20 minutes after 10 seconds shaking. The analysis were done twice in three replicates. To avoid catabolite repressing effect of glucose, for the pre-culture medium with galactose was used.

Medium of pre-culture MRS-galactose;
Medium of culture, MRS with 1% of the sugar tested
in each well; 300 µL of medium and 1% of pre-culture
OD measured each 20 minutes during 24 h after 10 seconds shaking The blank is represented by MRS without bacteria.

The results are shown in Table I below: (+) for the presence of growth (+/−) for a moderate growth and (−) for an absence of growth. Growth was considered as positive when the OD reached 0.8 or more.

| No | Sugar | Growth |
|---|---|---|
| 1 | D-ribose | + |
| 2 | D-galactose | + |
| 3 | D-fructose | + |
| 4 | D-mannose | + |
| 5 | L-sorbose | + |
| 6 | D-mannitol | + |
| 7 | D-sorbitol | − |
| 8 | D-cellobiose | + |
| 9 | D-maltose | + |
| 10 | D-lactose | + |
| 11 | D-saccharose | + |
| 12 | D-trehalose | + |
| 13 | dulcitol/galactitol | − |
| 14 | D-melezitose | − |
| 15 | Xylose | + |
| 16 | myo-inositol | − |
| 17 | D-melibiose | + |
| 18 | Gluconate | + |
| 19 | Galactosamine | − |
| 20 | Glucose | + |

Results:

*Lactobacillus mucosae* strain CNCM I-4429 has a specific pattern of sugar metabolisms. The pattern is completely different from those of *L. rhamnosus* or *L. paracasei* strains. Two sugars are not metabolized at all: melezitose and dulcitol.

Three sugars are very poorly and lately metabolized: galactosamine, myo-inositol and sorbitol. Four sugars are metabolized but lately: manitol, cellulose, sorbose and fructose.

EXAMPLE 2

Mucus Binding Properties of *Lactobacillus Mucosae* Strain CNCM I-4429

Adhesion to Mucin:

The assay of adhesion to mucin from porcin stomach type II (Sigma Aldrich) was performed by two protocols for studying biofilm formation, "static" and "dynamic".

First and last steps of preparation for both protocols were the same. Mucin was solved in PBS pH 7, in the concentration of 20 mg/ml, then the heat-sterilized glass spheres (6mm of diameter) were submerged in the mucin solution, incubated for 1 h at 37° C. and subsequently left overnight at 4° C. The day after the spheres were washed twice in PBS pH 7.

For the "static" protocol the spheres were submerged in 1 ml of overnight culture of *L. mucosae* grown in MRS+ glucose/MRS+ ribose and incubated for 4 h at 37° C., whereas in dynamic model each strain was incubated with glass spheres for 1 h at 37° C. before starting.

The dynamic model for studying biofilm formation was composed of two valve manifold 5-way (Sarstedt S. R. L., Verona, Italia) connected to each other with plastic tubing, connectors (PF 0052), and short drip chambers (PF 0047) equipped with onelead top covers (PF 0146), (Industrie Borla S.p.A., Moncalieri, Italia). All components were previously sterilized by immersion in ethanol (50%), and their assemblage with manifolds occurred in sterile conditions. In all tests three chambers, filled with the culture and 3 glass spheres were used. MRS broth (Oxoid) diluted in water (50%) and added with vancomycin (4 μg/ml), was used as medium to obtain the continuous flow (by gravity) into the chambers for 24 h. The temperature into the chambers was kept at 37° C. by using an external water bath. Subsequently the sphere was aseptically removed (in dynamic model twice: after 1 h-T0 and at the end of incubation-T24), washed twice in physiological saline solution to remove the non-adherent cells, submerged in 1 ml of physiological saline solution and vortexed for 1 minute to release the attached cells in solution. Then decimal dilutions were prepared and 100 μL of each dilution were spread into Petri plate containing MRS (Man, Rogosa, Sharpe) Agar medium.

The decimal dilutions were prepared as well from overnight cultures (for static protocol) and from medium present in the chambers—planktonic cells (in dynamic protocol), in order to determine the number of cells adhered. The plates were incubated at 37° C. for 24 h in anaerobic conditions.

The results are shown on Table II below:

TABLE II

| Adhesion to mucus of *L. mucosae* strains (static assay) | | |
|---|---|---|
| Strains/time | Liquid (cfu/ml) | T4 (cfu/ml) |
| Glucose | | |
| *L. mucosae* CNCM I-4429 | 7.55E+08 | 4.20E+06 |
| *L. mucosae* LMG 19534 T | 1.69E+08 | 2.20E+05 |
| *L. mucosae* 4 | 5.55E+08 | 2.00E+06 |
| *L. mucosae* 5 | 2.40E+08 | 1.70E+06 |
| Ribose | | |
| *L. mucosae* CNCM I-4429 | 1.50E+09 | 1.20E+05 |
| *L. mucosae* LMG 19534 T | 1.50E+06 | 2.00E+03 |

TABLE II-continued

| *L. mucosae* 4 | 4.50E+07 | 3.00E+04 |
|---|---|---|
| *L. mucosae* 5 | 1.70E+07 | 6.00E+04 |
| Adhesion to mucus of *L. mucosae* strains (dynamic assay) | | |
| Strains/time | T0 (cfu/cm2) | T24 (cfu/ml) |
| *L. mucosae* CNCM I-4429 | 1.6E+06 | 8.8E+04 |
| *L. mucosae* LMG 19534 T | 1.6E+03 | 5.4E+04 |
| *L. mucosae* 4 | 5.22E+04 | 5.2E+04 |
| *L. mucosae* 5 | 5.84E+04 | 3.0E+04 |

These results show that *Lactobacillus mucosae* strain CNCM I-4429 has a higher adhesion to mucus when compared to the 3 other *L. mucosae* strains.

Adhesion to Cell Monolayers:

The evaluation of adhesion to Caco2 and HT29 monolayers was performed twice in two replicates. The assays consisted of the 90 min incubation of *L. mucosae* ($10^7$ cfu $-10^8$ cfu) strains with the monolayer of cell lines composed of 500000 cells. *L. mucosae* strains were previously stained for 30 min with fluorescent probe 6CFDA. At the end of the incubation time, the monolayers were gently washed and the adhered microorganisms cells were lysed in order to quantify the fluorescence level and to determine the number of cells adhered to epithelium.

The results are shown on Table III below:

TABLE III

| HT-29 cells | | | |
|---|---|---|---|
| CNCM I-4429 | spread: $10^8$ cfu | adhered: | 3.00E+05 |
| Caco2 cells | | | |
| CNCM I-4429 | spread: $10^8$ cfu | adhered: | 4.00E+05 |

EXAMPLE 3

Antimicrobial Activity of *Lactobacillus Mucosae* Strain CNCM I-4429

The "overlay" method described in the literature (CHARTERIS et al., J Food Prot, 61, 1636-43, 1998; TOMINAGA & HATAKEYAMA, Appl Environ Microbiol, 72, 1141-7, 2006) has been used for the tests.

Cultures of 11 h, 18 h and 48 h hours of *Lactobacillus mucosae* CNCM I-4429 on glucose-containing medium were centrifuged and the acid pH of the supernatant (~pH 4) was adjusted with 2M NaOH to pH 6.5. In that way the lactic acid was neutralized and dissociated which removes its toxicity. The "overlay" test has been performed on plates. Medium used was Brain Heart Infusion—BHI (Difco) soft (0.7% agar), inoculated with an overnight culture of *Salmonella enterica*. When the medium surface after inoculation was dried, in each plate 4 wells of 5 mm diameter were punched. Then, 80 μl of cell-free supernatant (pH adjusted and non-adjusted for comparison) of *L.mucosae* was placed in each well.

Plates were incubated 24 h in anaerobic conditions at 37° C. Results were visualized and pictures of plates were taken. Experiments were repeated at least twice, mostly three times.

Figure 2:
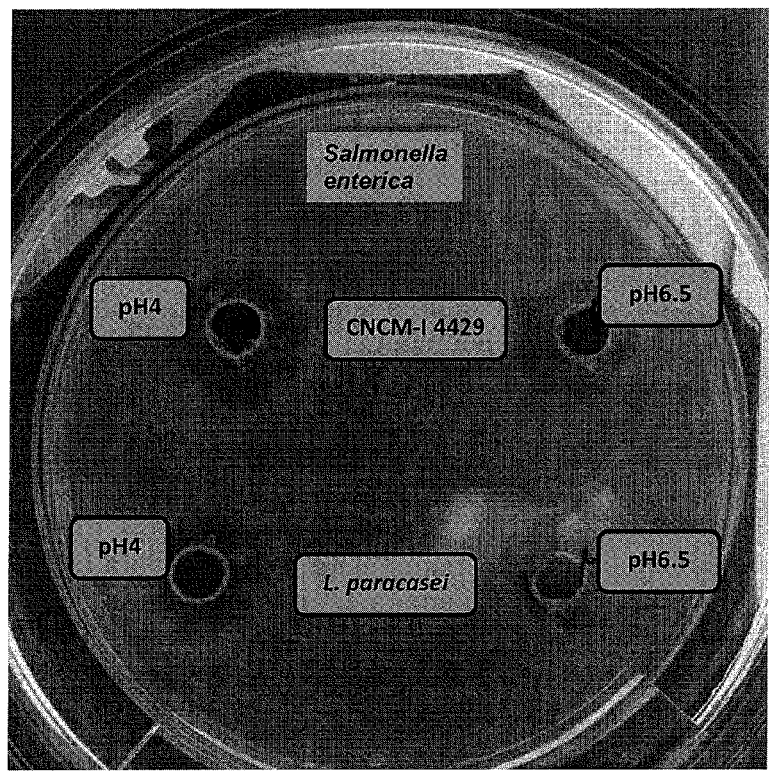
FIG. 2: Visualization of antimicrobial activity of *Lactobacillus mucosae* strain I-4429 on plates at 16 hours of cultures. On the left and on the top the inhibition of *Salmonella enterica* growth with the *L. mucosae* supernatant at pH4; On the right and on the top the pathogen growth inhibition with the neutralized (pH6,5) *L. mucosae* supernatant. On the bottom the inhibition of *Salmonella enterica* growth with the *L. paracasei* supernatant at pH4 (on the left) and pH6,5 (on the right).

The results of a representative experimentation with a culture of 16 hours are shown on FIG. 2: on the left and on the top the inhibition of *Salmonella enterica* growth with the *L. mucosae* supernatant at pH4; on the right and on the top the pathogen growth inhibition with the neutralized (pH6.5) *L.*

*mucosae* supernatant. On the bottom the inhibition of *Salmonella enterica* growth with the *L. paracasei* supernatant at pH4 (on the left) and pH6.5 (on the right).

For the *L. mucosae*, the sizes of the zone of inhibition are: at pH4=18 mm and, at pH6.5=16 mm. For the *L. paracasei*, the sizes of the zone of inhibition are: at pH4=16 mm and, at pH6.5=3 mm.

These results show that *L. mucosae* CNCM I-4429 exhibits a very strong growth inhibition of *Salmonella enterica* pathogen.

EXAMPLE 4

Effect of *Lactobacillus Mucosae* Strain CNCM I-4429 on the Transepithelial Resistance of Gut Epithelial Cells The effect of strain CNCM I-4429 on the transepithelial resistance of a monolayer of intestinal epithelial cells Caco2 was compared with those of diverse *L. casei* and *L. rhamnosus* strains including *L. casei* strain DN 114001 (CNCM I-1518) and *L. rhamnosus* strain LGG, which are both known for their ability to decrease the permeability of intestinal epithelial barrier (DONATO et al., 2010 and EUN et al., 2010, cited above).

Methods:

Caco2 cells were used. These cells are able to form a monolayer in in vitro conditions.

Cells are grown in minimal Eagle medium (modified by Dulbecco/Vogt DMEM, Invitrogen) containing 10% of serum (BioWhittaker), 1% of amino acids (Invitrogen) and 1% of penicillin/streptomycin (10 000 U/mL de penicillin, 10 000 µg/mL de penicillin/streptomycin (10 000 U/mL of penicillin, 10 000 µg/mL of streptomycin, Invitrogen). Cells are maintained at 37° C. in a humid atmosphere incubator with 5% of $CO_2$.

Twice a week cells are washed with PBS buffer without calcium and magnesium and diluted in a fresh medium. Then cells are trypsinated (Trypsine Invitrogen). The cell viability is checked with blue trypan exclusion test. 4 million cells are put in special flasks for cellular culture of 75 $cm^2$ (TPP).

Transwell plates (Sigma) are inoculated with $10^5$ cells in 0.5 ml of medium in both compartments.

In parallel bacteria are cultivated for 16 h at 37° C. in MRS medium.

After 6 days of cells incubation, when TEER is >1300 omega, the bacteria are put in contact with the cells. $10^6$ cfu of the bacteria to be tested added to the apical compartment of the Transwell chambers and are incubated with cells during 24 hours. For the experimentations performed in presence of TNF-α, it is added on the basal compartment of the Transwell chambers at 10 ng/ml, 3 hours after the bacteria. As a control, a Transwell chamber without addition of bacteria is used.

TEER is measured in the Transwell chambers with the voltimeter $Evom^2$ (World Precision Instruments) at $T_0$ and $T_{24}$. Experience was repeated 3 times independently. The evolution of the TEER during the experimentation is represented as the ratio: [TEER24h/TEERt0 cells treated with bacteria]/[TEER24h/TEERt0 control].

Figure 3:
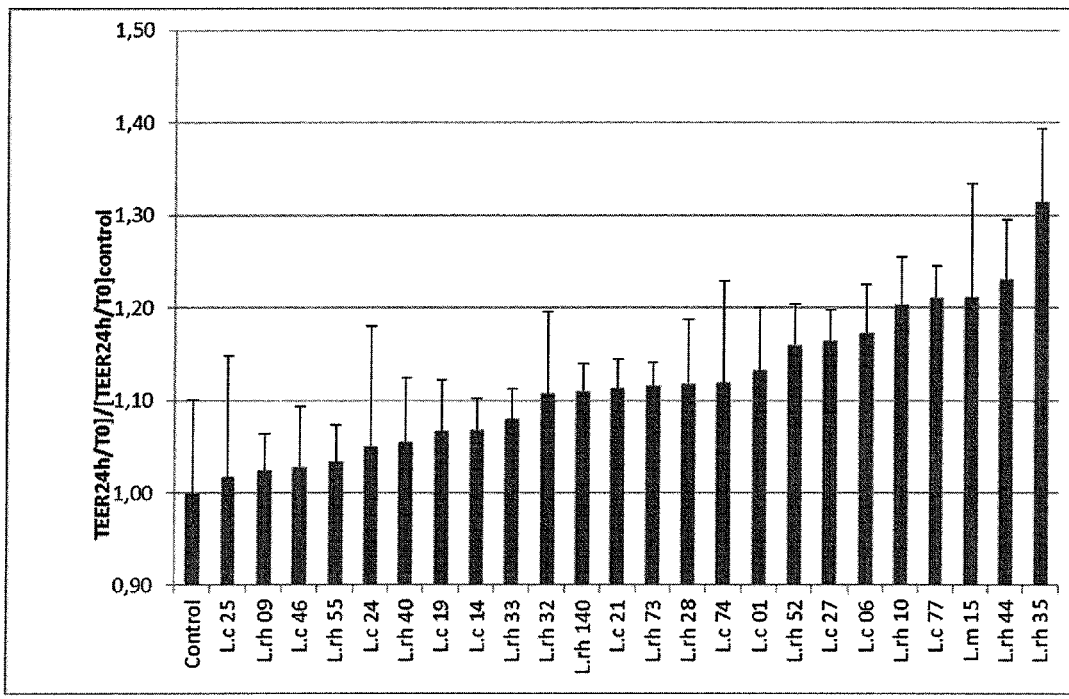
FIG. 3: Effects of tested bacteria on the transepithelial resistance of the cell monolayer in basal conditions. L.c indicates *L casei* strains, L.c 01 being strain CNCM I-1518; L.rh indicates *L. rhamnosus* strains, L. rh 35 being strain LGG; L.m 15 represents *L. mucosae* CNCM I-4429; the control is identified.
Figure 4:
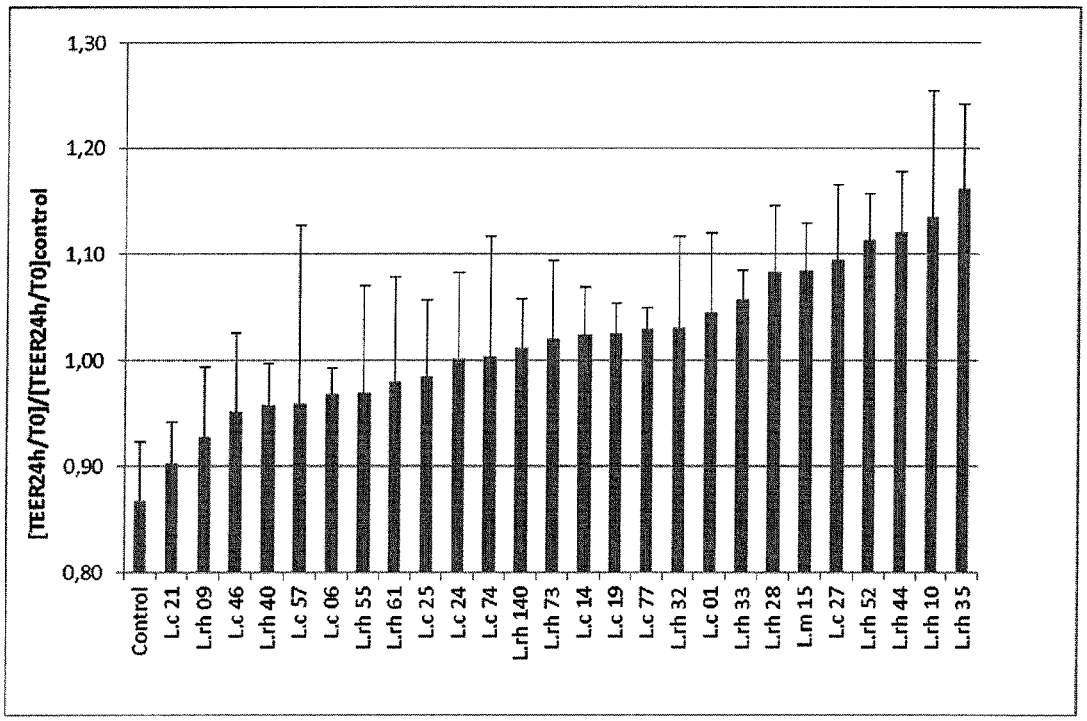
FIG. 4: Effects of tested bacteria on the transepithelial resistance of the cell monolayer after its destabilization with TNF-α. L.c indicates *L casei* strains, L.c 01 being strain CNCM I-1518; L.rh indicates *L. rhamnosus* strains, L. rh 35 being strain LGG; L.m 15 represents *L. mucosae* CNCM I-4429; the control is identified.

Results:

The results are shown in FIGS. 3 and 4.

FIG. 3 shows the effects of the tested bacteria on the transepithelial resistance of the cell monolayer in basal conditions. FIG. 4 shows their effects on the transepithelial resistance of the cell monolayer after its destabilization with TNF-α. L.c indicates *L casei* strains, L.c 01 being strain CNCM I-1518; L.rh indicates *L. rhamnosus* strains, L. rh 35 being strain LGG; L.m 15 represents *L. mucosae* CNCM I-4429; the control is identified.

The results of FIG. 3 show that in basal conditions *L. mucosae* CNCM I-4429 enhances the transepithelial resistance of about 21%. Under the same experimental conditions *L. rhamnosus* LGG enhances it of about 31% and *L. casei* CNCM I-1518 enhances it of about 13%.

The results of FIG. 4 show that after destabilization with TNF-α the transepithelial resistance of the control monolayer is lowered of 14% when compared to the basal conditions. In contrast, in cells incubated with *L. mucosae* CNCM I-4429 the transepithelial resistance is enhanced of about 8% when compared to the basal conditions. Under the same experimental conditions *L. rhamnosus* LGG enhances it of about 16% and *L. casei* CNCM I-1518 enhances it of about 5%.

EXAMPLE 5

Effect of *Lactobacillus Mucosae* Strain CNCM I-4429 on Distribution of ZO-1 in a Monolayer of Gut Epithelial Cells ZO-1 is an intracellular tight junction scaffolding protein, which plays an important part in the integrity of tight junctions and the imperviousness of the TJ epithelia.

The distribution of ZO-1 in the Caco2 cells monolayers used in Example 4 was studied by immunofluorescence, under basal conditions or after treatment with TNF-α with or without preincubation with *lactobacilli*, as disclosed in Example 4. The effect of *L. mucosae* CNCM I-4429 on ZO-1 subcellular distribution was compared with the effect of *Lactobacillus casei* strain L.c 21, which has no effect on enhancement of transepithelial resistance (FIG. 4).

Figure 5:
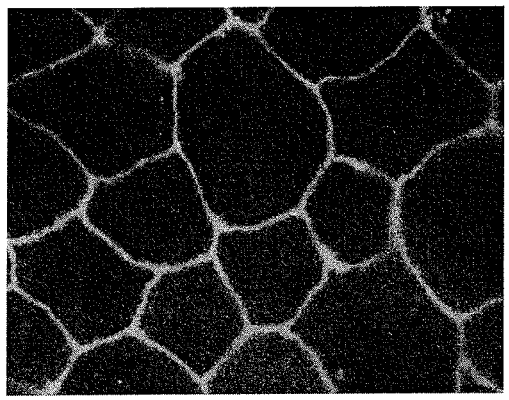
FIG. 5: Effects of *Lactobacillus mucosae* strain I-4429 on distribution of ZO-1 in a monolayer of gut epithelial cells. A: Caco2 cells monolayer under basal conditions; B: Caco2 cells monolayer treated with TNF-α; C: Caco2 cells monolayer treated with TNF-α in presence of L.c 21; D: Caco2 cells monolayer treated with TNF-α in presence of CNCM I-4429.
Figure 5:
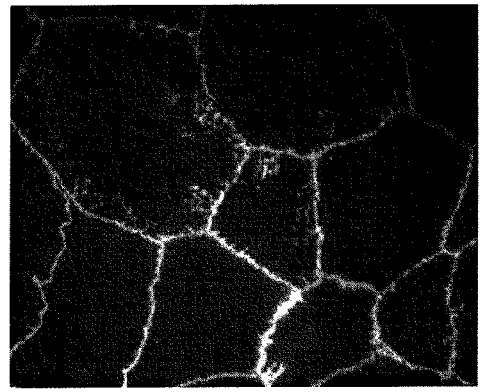
Figure 5:
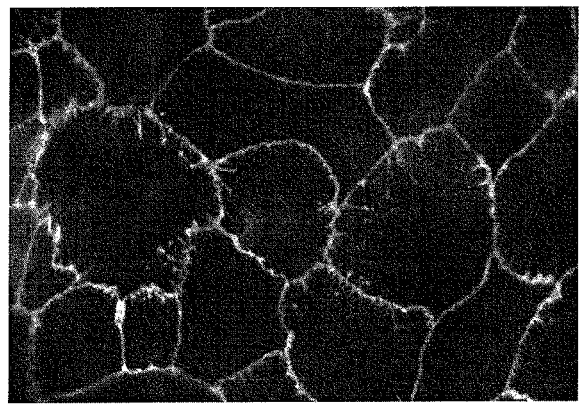
Figure 5:
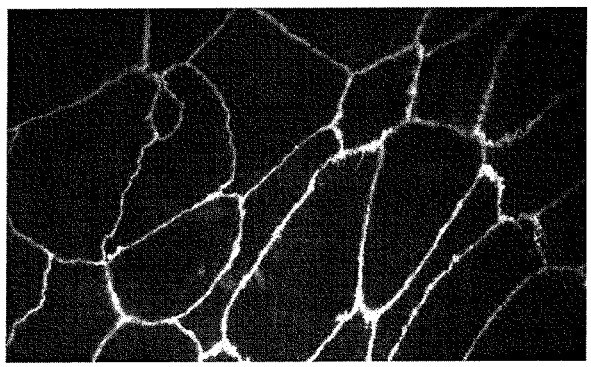

The results are shown on FIG. 5: A: Caco2 cells monolayer under basal conditions; B: Caco2 cells monolayer treated with TNF-α; C: Caco2 cells monolayer treated with TNF-α in presence of L.c 21; D: Caco2 cells monolayer treated with TNF-α in presence of CNCM I-4429.

Under basal conditions, ZO-1 is mainly localized at the membrane of cells; treatment by TNF-α induces a disorganization of ZO-1, shown by the presence of diffuse intracytoplasmic structures. These structures are also present in TNF-α-treated cells incubated with L.c 21, while TNF-α-treated cells incubated with CNCM I-4429 show almost the same pattern of distribution of ZO-1 as cells under basal conditions.

The invention claimed is:

1. An isolated *Lactobacillus mucosae* strain deposited with the CNCM (Collection Nationale De Cultures De Microorganismes) under Accession number I-4429.

2. A composition comprising a *Lactobacillus mucosae* strain of claim 1.

3. The composition according to claim 2, wherein the composition is a food product.

4. A pharmaceutical composition comprising a *Lactobacillus mucosae* strain of claim 1.

* * * * *